United States Patent [19]

Louderback

[11] Patent Number: 4,668,630

[45] Date of Patent: May 26, 1987

[54] STABILIZED ENZYMATIC COMPOSITION

[75] Inventor: Allan L. Louderback, Temple City, Calif.

[73] Assignee: Beckman Instruments, Inc., Fullerton, Calif.

[21] Appl. No.: 656,806

[22] Filed: Oct. 1, 1984

[51] Int. Cl.[4] .......................... C12N 9/99; C12N 9/96; C12Q 1/28

[52] U.S. Cl. ...................................... 435/184; 435/29; 435/188; 435/810

[58] Field of Search ....................... 435/19, 21, 15, 17, 435/26, 188, 810, 184

[56] References Cited

U.S. PATENT DOCUMENTS 3,956,069 5/1976 Allain et al. .......................... 435/26

FOREIGN PATENT DOCUMENTS 0009222 4/1980 European Pat. Off. ............ 435/188

OTHER PUBLICATIONS

C. Abstracts I: 68:103355c *Clin. Chim. Acta* 20(1) 7–10.
Chemical Abstracts II: 99:171969w *Int. J. Biochem.* 1983, 15(10), 1279–1282.
Chemical Abstracts III: 97:19656t *Biochem. J.* 1982, 202(3), 581–587.

*Primary Examiner*—Christine M. Nucker
*Attorney, Agent, or Firm*—W. H. May; Arnold Grant; Julia E. Abers

[57] ABSTRACT

An improved composition of the type comprising a known concentration of at least one enzyme. The composition is characterized in that substantially all of at least one of the enzymes is combined with a stabilizing amount of a reversible inhibitor thereof to form an inhibitor-enzyme complex, thereby stabilizing the enzyme moiety of the complex.

A method of stabilizing a composition comprising a known concentration of at least one enzyme. The method comprising combining substantially all of at least one of the enzymes with a stabilizing amount of a reversible inhibitor thereof to form an inhibitor-enzyme complex, thereby stabilizing the enzyme moiety of the complex.

6 Claims, No Drawings

STABILIZED ENZYMATIC COMPOSITION

BACKGROUND OF THE INVENTION

1. Field of the Invention

This invention relates to a laboratory material and, more particularly, to a composition comprising a known concentration of at least one enzyme.

2. Description of the Prior Art

Recently, there has been extensive research in the art of liquid compositions comprising stabilized enzymes for use in a clinical laboratory. These stabilized liquid compositions have included standards, calibrators, and controls (1–5) as well as reagents (6–10).

Because of the extreme importance in providing reliable enzymatic compositions for use in conjunction with clinical laboratory assays, much effort is still being expended in the further development of stabilized enzymatic products in order to continually improve the reliability of clinical assays.

SUMMARY OF THE INVENTION

The instant invention encompasses a stabilized enzymatic composition for use in the clinical laboratory. The composition of the present invention is of the type which comprises a known concentration of at least one enzyme. The present composition is characterized in that substantially all of at least one such enzyme is combined with a stabilizing amount of a reversible inhibitor thereof to form an inhibitor-enzyme complex, whereby the enzyme moiety of such complex is stabilized.

The present invention also encompasses a method of stabilizing an enzymatic composition comprising a known concentration of at least one enzyme. The method comprises combining substantially all of at least one such enzyme with a stabilizing amount of a reversible inhibitor thereof to form an inhibitor-enzyme complex, whereby the enzyme moiety of the complex is stabilized.

Still other features and attendant advantages of the present invention will become apparent to those skilled in the art from a reading of the following detailed description of the preferred embodiments.

DESCRIPTION OF THE PREFERRED EMBODIMENTS

The enzymatic composition of the instant invention comprises at least one enzyme constituent of known value. In the case of standards, calibrators, and controls, any enzyme of clinical significance can be present therein. Typical enzymes which are currently assayed in clinical laboratories include acid phosphatase (ACP); aldolase, alkaline phosphatase (ALP); amylase; esterase; creatinine kinase ((CK); also known as creatinine phosphokinase (CPK)); $\gamma$-glutamyl transpeptitase ($\gamma$-GT; GGT); $\alpha$-hydroxy buturic dehydrogenase ($\alpha$-HBD; HBD); isocitric dehydrogenase (ICD); lactic dehydrogenase (LDH); glucine amino peptidase (LAT); lipase; alanine amino transferase (SGPT; ALT; GPT; glutamic pyruvic transaminase); and aspartate amino transferase (SGOT; AST; GOT; glutamic-oxyl acetic transaminase).

In the case of enzymatic reagents, any enzyme capable of use in an enzymatic reaction can be present therein. Such enzymes, in addition to those listed above, include, but are not limited to, glycerol kinase; glycerol phosphate dehydrogenase (G-1-PDH); pyruvate kinase (PK); maltose phosphorylase (MP); beta-D-phosphoglucomutase (beta-PGM); glucose-6-phosphate dehydrogenase (G-6-PDH); and glucose dehydrogenase.

The activity of each enzyme present in the composition in the absence of the inhibitor is not critical. In the case of standards, calibrators, and controls, the activity of each enzyme, in the absence of the inhibitor, should be within a range covering both normal and abnormal values. In the case of a reagent, the enzyme activity, in the absence of the inhibitor, should be such that the reagent can perform the assay for which it is designed.

Reversible inhibitors include, but are not limited to, malonate and pyrophosphate (competitive inhibitor for succinate); fluorocitrate (competitive inhibitor for citrate); oximate (competitive inhibitor for L-lactate); long chain fatty acid amides (competitive inhibitor for alcohols, essentially ethanol); monoguanidines (competitive inhibitor for monoamines); diguanidines (competitive inhibitor for diamines); substituted tetraalkyl-ammonium compounds (competitive inhibitors for acetylcholine); sulfonamides (competitive inhibitor of p-aminobenzoate); folic acid analogs (competitive inhibitor of folate); pyridine-3-sulfonate (competitive inhibitor of nicotinic acid); riboflavin monosulfate (competitive inhibitor of riboflavin monophosphate); and deoxypyridoxine phosphate (competitive inhibitor of pyridoxyl-P).

The enzymatic composition of this invention can also further comprise other materials typically found in controls, standards, or reagents. For example, in the case of controls, calibrators or standards, the enzymatic composition can also further comprise metabolites, electrolytes, and hormones of known value. In the case of reagents, the enzymatic composition can further comprise co-enzymes, ions, and chromogens.

In general, the composition of the instant invention can be prepared via techniques customarily employed for preparing controls, calibrators, standards, and reagents, as applicable. The only additional step would entail the addition of the desired reversible inhibitors at a convenient point in the manufacturing process.

The reversible inhibitor can be removed from the enzyme either prior to use or in situ in a reaction medium via any number of techniques. For example, the inhibitor can be removed by using another enzyme to digest away the inhibitor thus freeing the stabilized enzyme. Alternatively, one could use an anti-factor system to bind with active groups on the enzyme and thereby toss off the inhibitor (e.g., adding extra —SH groups with a thiol binding agent such as cystine, N-ethyl-maleimide, or p-Cl-mercurobenzoate).

In addition, the inhibitor can be removed physically, e.g., by passing the enzyme-inhibitor system through a column system to selectively remove the inhibitor thereby yielding a column eluant containing an active enzyme.

The inhibitor can also be removed from the inhibitor-enzyme complex by subjecting the complex to an electrophoretic field.

In one preferred embodiment, LD isoenzymes are stabilized by a reversible inhibitor selected from the group consisting of salts of oxalic acid, salts of oxamic acid, and mixtures thereof. Typical salts of such acids include, but are not limited to, alkali metal salts. Preferably, salts of such acids are selected from the group consisting of sodium and potassium salts thereof and mixtures thereof. More preferably, the reversible inhibitor is selected from the group consisting of potassium oxalate, sodium oxamate, and mixtures thereof. Also, preferably, up to 30, more preferably from about 4 to about 20, and optimally from about 5 to about 10, mg/ml inhibitor is employed in this embodiment.

The following examples are provided for the purpose of further illustration only and are not intended to be limitations on the disclosed invention.

EXAMPLES 1-9

LD Stability Study

To 100 ml of a lactate dehydrogenase serum ethylene glycol (LD SEG) solution (i.e., a solution formed by adding 33% ethylene glycol to a concentrated human serum) was added 2.0 gm of potassium oxalate ($KO_2C$-$CO_2K$) to form a base solution. Aliquots of this base solution were diluted as shown in Table I with a LD SEG solution devoid of $KO_2CCO_2K$.

TABLE I

| | Base Solution, ml (LD SEG + 20 mg/ml $KO_2CCO_2K$) | LD SEG | Serial Dilution, mg/ml $KO_2CCO_2K$ |
|---|---|---|---|
| 1 | 10 | 0 | 20 |
| 2 | 5 | 5 | 10 |
| 3 | 3.5 | 6.51 | 7 |
| 4 | 2.5 | 7.5 | 5 |
| 5 | 2 | 8 | 4 |
| 6 | 1.5 | 8.55 | 3 |
| 7 | 1 | 9 | 2 |
| 8 | 0.5 | 9.5 | 1 |
| 9 | 0 | 10 | 0 |

The LD activity of each of the serial dilution samples was measured on a Roche Cobas brand UV clinical analyzer and the results are set forth in Table II.

TABLE II

| Example | Serial Dilution, mg/ml $KO_2CCO_2K$ | LD, IU/l |
|---|---|---|
| 1 | 20 | 30.84 |
| 2 | 10 | 50.37 |
| 3 | 7 | 61.31 |
| 4 | 5 | 74.22 |
| 5 | 4 | 81.46 |
| 6 | 3 | 91.97 |
| 7 | 2 | 97.02 |
| 8 | 1 | 113.29 |
| 9 | 0 | 131.07 |

Table II shows the inhibition of LD activity by $KO_2CCO_2K$.

One portion of each serial dilution was then stored at 25° C. and another portion at −20° C. for a three day period. At the end of this three day period an aliquot of each stored sample was taken, applied to a Beckman Instruments, Inc. Paragon TM brand LD gel. The gel was electrophoresed (thereby removing the inhibitor) and then developed with a Beckman Instruments, Inc. Paragon TM brand LD reagent. The results of this stability study are set forth in Table III.

TABLE III

| Example | Serial Dilution, mg/ml $KO_2CCO_2K$ | Storage Temp, °C. | LD1 | LD2 | LD3 | LD4 | LD5 |
|---|---|---|---|---|---|---|---|
| 1 | 20 | 25 | 27.1 | 47.3 | 16.9 | 4.4 | 4.3 |
| 1 | 20 | −20 | 26.5 | 38.9 | 19.2 | 5.5 | 9.8 |
| 2 | 10 | 25 | 26.8 | 46.6 | 18.7 | 4.2 | 3.7 |
| 2 | 10 | −20 | 24.1 | 37.6 | 20.7 | 8.1 | 9.6 |
| 3 | 7 | 25 | 29.9 | 49.7 | 17.8 | 1.7 | 1.0 |
| 3 | 7 | −20 | 25.6 | 39.1 | 20.7 | 6.4 | 8.2 |
| 4 | 5 | 25 | 28.6 | 47.2 | 18.4 | 2.6 | 3.3 |
| 4 | 5 | −20 | 25.0 | 38.3 | 20.5 | 7.1 | 9.0 |
| 5 | 4 | 25 | 30.2 | 51.4 | 16.6 | 0.9 | 1.0 |
| 5 | 4 | −20 | 25.9 | 43.0 | 20.9 | 4.8 | 5.4 |
| 6 | 3 | 25 | 33.2 | 50.7 | 15.7 | 0.5 | 0.0 |
| 6 | 3 | −20 | 26.6 | 41.8 | 20.9 | 5.1 | 5.5 |
| 7 | 2 | 25 | 34.4 | 49.6 | 12.9 | 3.1 | 0.0 |
| 7 | 2 | −20 | 27.2 | 40.5 | 20.7 | 5.4 | 6.1 |
| 8 | 1 | 25 | 36.0 | 48.3 | 12.2 | 3.0 | 0.5 |
| 8 | 1 | −20 | 28.2 | 40.2 | 20.7 | 5.1 | 5.3 |
| 9 | 0 | 25 | 37.1 | 49.7 | 8.1 | 4.0 | 1.0 |
| 9 | 0 | −20 | 32.9 | 47.3 | 17.9 | 0.3 | 1.3 |

Examples 1 through 8 of Table III depict the improved stability obtained via one embodiment of the stabilized compositions of the present invention. Based on this disclosure, many other modifications and ramifications will naturally suggest themselves to those skilled in the art. These are intended to be within the scope of this invention.

Bibliography

1. U.S. Pat. No. 3,876,375
2. U.S. Pat. No. 4,121,905
3. U.S. Pat. No. 4,201,694
4. U.S. Pat. No. 4,288,343
5. U.S. Pat. No. 4,325,832
6. U.S. Pat. No. 4,250,254
7. U.S. Pat. No. 4,271,264
8. U.S. Pat. No. 4,277,562
9. U.S. Pat. No. 4,282,316
10. U.S. Pat. No. 4,310,625

The embodiments of the invention in which an exclusive property or privilege is claimed are defined as follows:

1. A method for stabilizing for storage and subsequently restoring activity a known concentration of the enzyme lactate dehydrogenase in a composition, said method comprising the steps of:
    adding an oxalic acid salt to said composition as a reversible inhibitor of said lactate dehydrogenase; and,
    forming a stable inhibitor-enzyme complex between said oxalic acid salt and said lactate dehydrogenase, thereby stabilizing the enzyme moiety of the complex,
    removing said oxalic acid salt from said inhibitor-enzyme complex to restore the enzyme activity.

2. The method of claim 1 wherein said oxalic acid salt is potassium oxalate.

3. The method of claim 1 wherein said salts are alkali metal salts.

4. The method of claim 2 wherein said potassium oxalate is present in an amount up to 30 mg/ml.

5. The method of claim 2 wherein said potassium oxalate is present in an amount from about 4 to about 20 mg/ml.

6. The method of claim 2 wherein said potassium oxalate is present in an amount from about 5 to about 10 mg/ml.

* * * * *